United States Patent [19]
Lindenberg et al.

[11] Patent Number: 5,433,723
[45] Date of Patent: Jul. 18, 1995

[54] APPARATUS FOR WIDENING A STENOSIS

[75] Inventors: Josef Lindenberg; Wolfram Schnepp-Pesch, both of Karlsruhe, Germany

[73] Assignee: Angiomed AG, Karlsruhe, Germany

[21] Appl. No.: 202,468

[22] Filed: Feb. 28, 1994

Related U.S. Application Data

[63] Continuation of Ser. No. 959,615, Oct. 13, 1992, abandoned.

[30] Foreign Application Priority Data

Oct. 11, 1991 [DE] Germany .................. 41 33 696.8
Mar. 10, 1992 [DE] Germany .................. 42 07 557.2

[51] Int. Cl.⁶ .............................................. A61M 29/00
[52] U.S. Cl. .................................. 606/198; 623/1; 623/12
[58] Field of Search ............... 606/108, 191, 195, 198, 606/200; 604/96, 104–109, 127, 128; 623/1, 11, 12; 128/899

[56] References Cited

U.S. PATENT DOCUMENTS

| | | |
|---|---|---|
| 4,665,918 | 5/1987 | Garza et al. |
| 4,681,110 | 7/1987 | Wiktor |
| 4,990,155 | 2/1991 | Wilkoff ................. 606/191 |
| 5,002,556 | 3/1991 | Ishida et al. ........... 606/191 |
| 5,217,484 | 6/1993 | Marks ................... 128/899 |

FOREIGN PATENT DOCUMENTS

| | | |
|---|---|---|
| 0380668 | of 0000 | European Pat. Off. |
| 0411118 | 3/1988 | European Pat. Off. |
| 2617721 | 7/1987 | France |

Primary Examiner—Peter A. Aschenbrenner
Assistant Examiner—William Lewis
Attorney, Agent, or Firm—Antonelli, Terry, Stout & Kraus

[57] ABSTRACT

The invention relates to an apparatus for widening a stenosis in an elongated body cavity such as an artery, the urethra, the ureter, a bile duct or the like, characterized by an endoprosthesis made from a memory alloy with a substantially cylindrical jacket-like outer contour with a lock surrounding and radially holding together the endoprosthesis and with an applicator for the endoprosthesis. It is important that the apparatus is supplied in such a way that in the delivery pack the endoprosthesis is held radially from the outside in its compressed (low temperature) position, which is ensured by the above-described construction of the apparatus according to the invention.

15 Claims, 4 Drawing Sheets

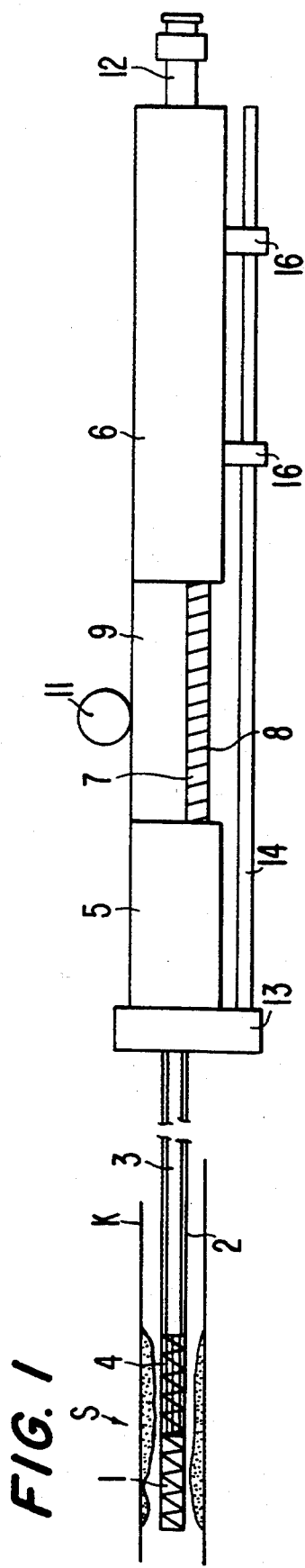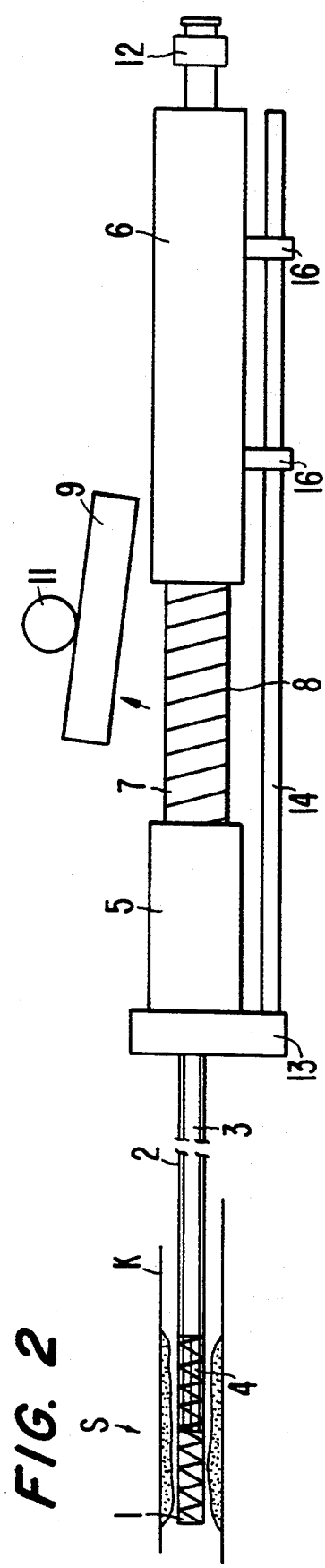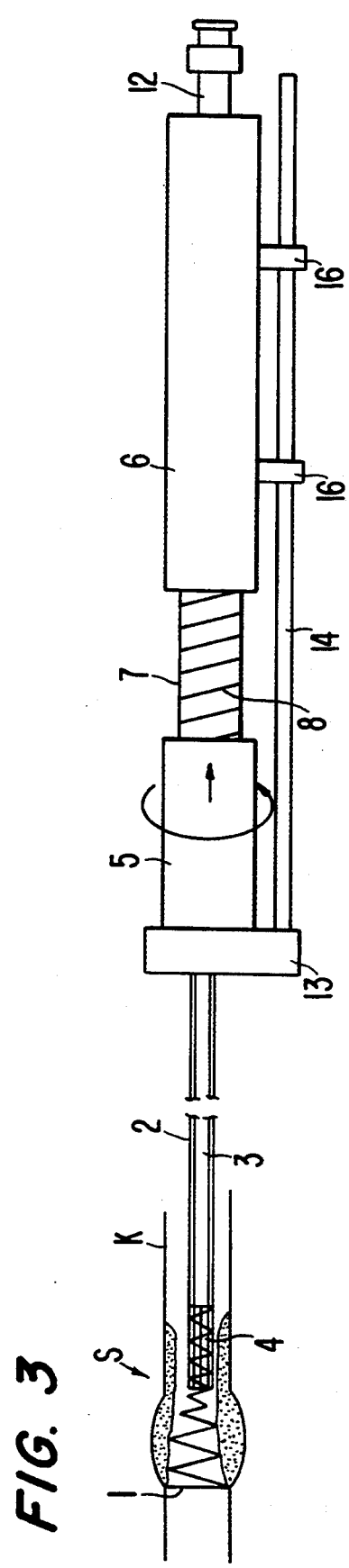

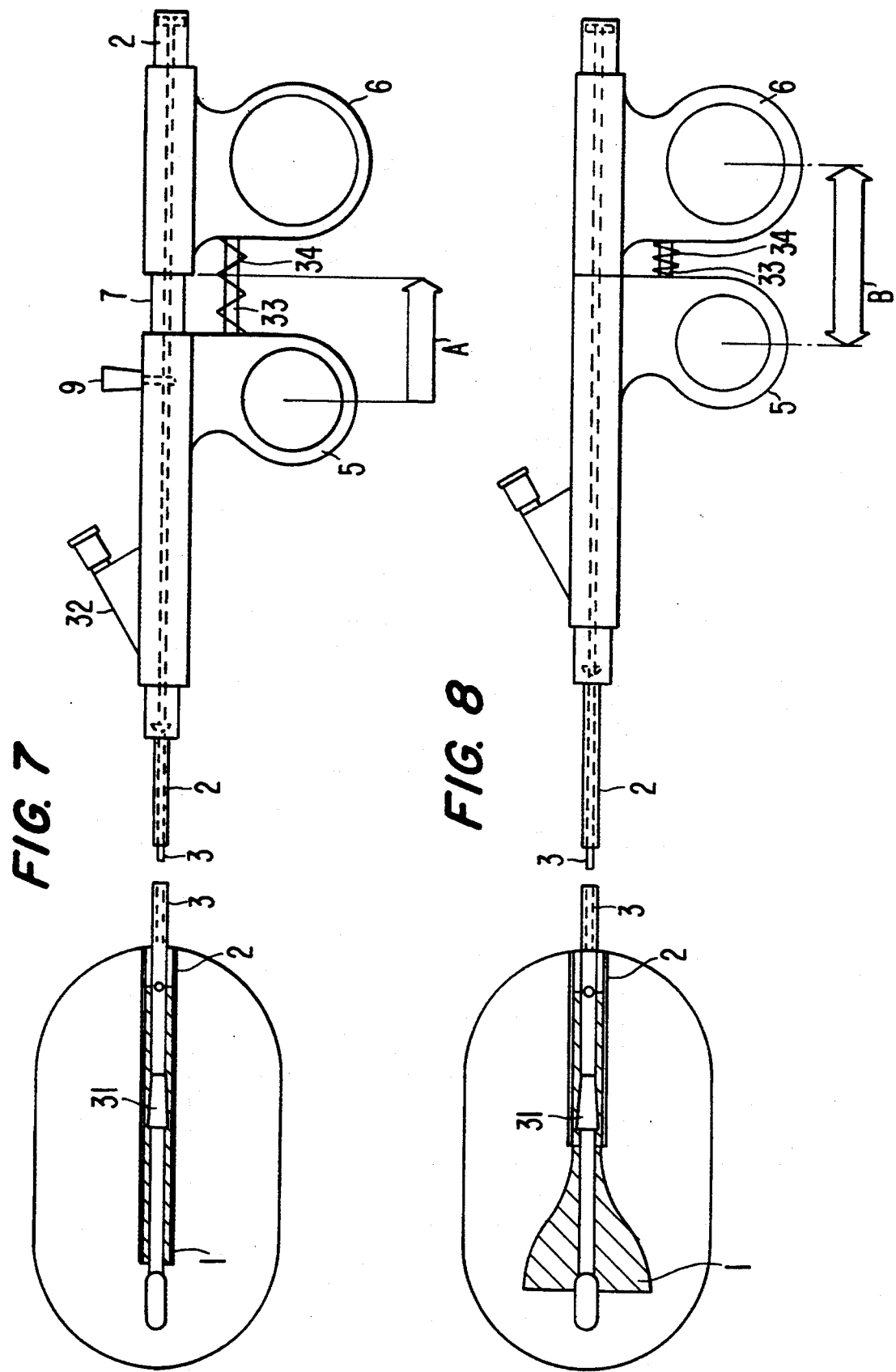

APPARATUS FOR WIDENING A STENOSIS

CROSS-REFERENCE TO RELATED APPLICATIONS

This application is a Continuation Application of Ser. No. 959,615, filed Oct. 13, 1992, now abandoned.

FIELD OF THE INVENTION

The present invention relates to an apparatus for widening a stenosis in a body cavity such as an artery, bile duct, ureter, urethra or the like.

BACKGROUND OF THE INVENTION

An occlusion or obstruction in an elongated body cavity such as in a vessel especially in an artery, is generally initially widened in that deposits such as plaque are removed, for example, by cutting out and suctioning or the like. However, this cannot take place up to the tissue material of the vessel because, at this point, there is a risk of injury.

If there is only a narrowing, for example, a stenosis, but not a complete occlusion, such as, for example, with an enlarged prostrate in the vicinity of the urethra, or after a certain through-flow area has been created in the previously complete occlusion, a radial widening of the stenosis is desired. Therefore, this is carried out not only in blood vessels, but also in other body passages or tubes such as the ureter, urethra, bile ducts, etc.

Previously, this function has been fulfilled by a balloon catheter, optionally with a double internal diameter, which brings about an instantaneous radial widening. This widening of the stenosis should remain permanently after the removal of the balloon catheter, but this is generally not the case. Therefore, permanent widening of a stenosis has already been proposed. Thus, a widening part is mounted on a balloon catheter in an axially fixed manner, with the widening part being introduced with the catheter and, by widening action, the catheter is plastically deformed in such a manner that the radial dimensions of the widening part increase and the widening part is pressed into the stenosis wall and, after releasing the air from the catheter, the catheter can be removed again, whereas, the widening part, in the plastically deformed state, remains in its location. For this purpose, a proposal has already been made for a sleeve in the form of an "optionally perforated" plastic or tissue-compatible metal envelope.

A significant disadvantage of the above proposed process resides in the fact that the sleeve must be introduced into the stenosis resting on the outer circumference of a catheter. First, the axial fixing is complicated and can either not be reliably achieved, so that the part can be left behind on advancing the catheter or a separate release of the part from the catheter causes problems. In addition, a widening part located externally on the catheter can lead to tissue damage. Finally, the widening through the balloon catheter in the case of such a part must initially lead to a radial extension, which is well beyond that which is ultimately desired for the widening part, because such parts, such as conventional compatible materials, to the extent that they have an adequate strength to maintain the stenosis open, have a considerable elastic deformation range, before there is a permanent plastic deformation to the desired radius. This more particularly occurs if the stenosis or the surrounding tissue material is pressed radially from the outside against the widening part.

SUMMARY OF THE INVENTION

The aim underlying the present invention essentially resides in providing an apparatus for widening a stenosis which, while avoiding the aforementioned disadvantages, allows a simple, problem-free and reliable widening of a stenosis in a short time.

According to the invention, an apparatus for widening a stenosis in a body cavity such as an artery, urethra, ureter, a bile duct or the like is provided which includes an endoprosthesis from a memory alloy with a substantially cylindrical jacket-like outer contour, a sleeve surrounding and radially holding together the endoprosthesis, and an endoprosthesis applicator.

The shape memory alloy endoprosthesis can be constructed in different ways. It may be a sheet spirally wound in its low temperature position, which widens into a cylindrical jacket in the high temperature position. It may be an expanded metal which has rhombic or honeycomb openings, it may be a helically wound wire part, in which optionally the individual turns are provided with axially parallel outward bends, which are, in each case, fixed to an adjacent turn by soldering, with the strength of the connections being below the tensile strength of the wire forming the endoprosthesis, but preferably above the bending forces, in particular in order to bring about helix lengthening. In addition, the endoprosthesis may be made from fabrics such as crosswoven fabrics, or knitted fabrics, such as, in particular, traverse warp circular knitted fabrics. Finally, an endoprosthesis may be formed with an axially parallel connecting part or spine, from which, to either side, extend arcuate ribs, which are, in each case, axially displaced from one side to the other, so that free ends of the ribs engage between one another.

According to further features of the present invention, the applicator and endoprosthesis are arranged in at least a partially axially overlapping manner, with the applicator being positioned radially between the sleeve and the endoprosthesis and, in particular, with the applicator at its end and, in particular, over the length by which it engages over the endoprosthesis being constructed in an axially split manner, for example, in such a manner that the applicator has tongues at an end thereof, which are axially separated from one another by slots. Thus, following the introduction of the endoprosthesis surrounded by the sleeve into the stenosis, for example, at the application point, the sleeve is retracted relative to the applicator without drawing the endoprosthesis with it and is therefore removed again from its application point. The endoprosthesis is held by the applicator and, as a result of its split construction with the individual tongues, the tongues can adapt to the successive widening of the endoprosthesis by the retraction of the sleeve. The applicator can finally be removed without drawing with the applicator or lengthening the endoprosthesis, because, following removal of the sleeve, the endoprosthesis is held on by the wall of the cavity or vessel and the frictional forces acting there are higher than those between the applicator tongues and the endoprosthesis.

According to another development of the present invention, a counter holder is engageable on a rear face of the endoprosthesis.

In all cases, the internal diameter of the sleeve is not less than the external diameter of the endoprosthesis in its low temperature state, for example, in its state below ambient temperature, as from which the endoprosthesis widens in its high temperature state. The counter holder or slide optionally has a diameter substantially corresponding to the endoprosthesis in its low temperature state.

It is also significant in the present invention that, prior to the introduction at the application point, the endoprosthesis is reliable and firmly radially held from the outside in its compressed low temperature position, which is ensured by the sleeve surrounding it. In order to avoid an unintentional or even only a partial sliding out of the endoprosthesis from the sleeve prior to the application of the endoprosthesis at its application point and which would make further use impossible, a further feature of the present invention resides in the sleeve and the applicator or counter holder being detachably axially blocked. For this purpose, a detachable blocking element for axially blocking the sleeve and the applicator is provided.

According to an advantageous further development of the present invention, the sleeve and the applicator are provided with handles or grips movable axially relative to one another.

According to an extremely simple construction in accordance with the present invention, the blocking element is positioned between the two handles and the blocking element is a spacer removably arranged between the handles.

In order to reliably maintain the endoprosthesis at the application point by the applicator which is held by its handle and so as to ensure that there is no relative movement of the applicator on the removing block, in accordance with further features of the present invention, the sleeve is axially displacable relative to the handle connected to the applicator by a turning movement of the handle connected thereto and, according to a particularly preferred development, an axial guide can be provided for the handle connected to the sleeve relative to the handle connected to the applicator.

According to further developments of the present invention, the applicator and parts fixed thereto have a hollow construction. As a result, a guide wire can be moved through the entire apparatus or, following the placing of a guide wire, the apparatus can be introduced into the vessel to be treated and for the purpose of bringing about its stenosis by a guide wire. In a further construction, at the rear end of the applicator or a part fixed thereto (handle), an adapter is provided, as a result of which a syringe can be fitted enabling the injection to take place of, for example, a plaque-dissolving agent (streptokinase), should this be necessary.

According to a preferred simple and easily applicable construction, the applicator extends into the endoprosthesis and is axially split at its front end. Furthermore, in a construction in which is has tongues at its end which are axially separated from one another by slots, the tongues have a radially outwardly directed projection.

According to a further development, a suction connection is constructed at the rear end of the sleeve.

BRIEF DESCRIPTION OF THE DRAWINGS

The invention is described in greater detail hereinafter relative to the non-limitative embodiments in connection with the accompanying drawings, wherein:

FIG. 1 is a schematic view of a first embodiment of the inventive apparatus for the introduction into a stenosis region of a blood vessel;

FIG. 2 is a schematic view of the apparatus of FIG. 1 with a spacer thereof removed between the applicator handle and handle of the envelope surrounding it;

FIG. 3 is a schematic view of the positioning of the endoprosthesis by retracting the envelope radially holding the endoprosthesis;

FIG. 7 is a schematic view of another embodiment of the inventive apparatus for introduction into a stenosis region of a blood vessel, with a forward end thereof being illustrated on an enlarged scale; and FIG. 8 is a schematic view of the embodiment of FIG. 7 with an endoprosthesis partially moved out of the sleeve.

DETAILED DESCRIPTION

Figure 4:
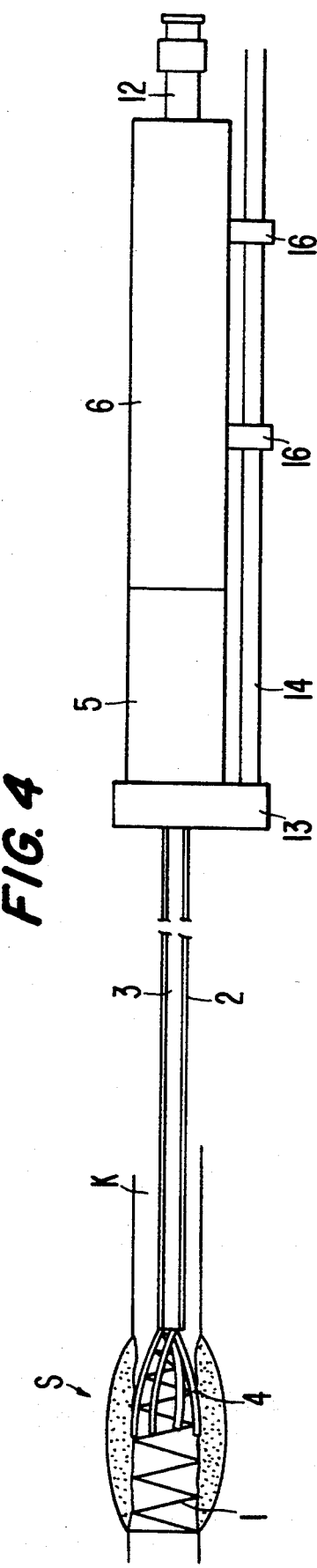
FIG. 4 is a schematic view of an end position following a complete retraction of the sleeve or envelope with the widened front split end of the applicator.
Figure 5:
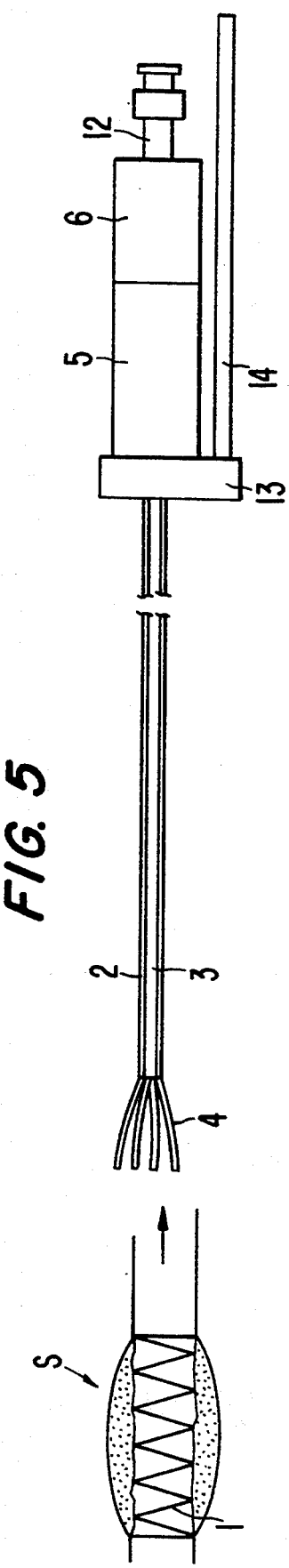
FIG. 5 is a schematic view of the endoprosthesis in position in the stenosis following the removal of the envelope and the applicator.

The inventive apparatus for widening a stenosis in a body cavity includes an endoprosthesis 1 fashioned of a shape memory alloy such as Ti—Ni, Al—Ni, Cu—Zn, commercially available under the names Nitinol, Biometal, or Memotal. The endoprosthesis 1, having a small radial diameter, is enveloped by a sleeve 2, as shown in FIG. 1, and has a substantially cylindrical outer contour in this position. In the drawing, the endoprosthesis 1 is diagrammatically shown as a helically wound wire; however, as can readily be appreciated, it may have numerous different shapes, such as a spirally rolled metal sheet, which is modified into a widened cylindrical jacket on widening from the low into the high temperature position. It could be made from a cylindrical jacket-like expanded metal, may be in the form of a circular woven fabric (cross-woven fabric) or knitted fabric (traverse warp circular knitted fabric). It may be rib-like with an axially parallel spine or connecting web, from which extend, in part, in a ring-like manner, bent ribs. The ribs may be oriented to the connecting web at right angles or at an angle diverging from the latter such as an angle of 50° to 70°. Preferably, the ribs, extending in opposite directions from the connecting web, are reciprocally axially displaced, so that the free ends of the ribs on one side may be, in each case, engaged between free ends of the ribs extending to the other side.

If the endoprosthesis has a helical construction, it may be provided with axially parallel oriented outwardly extending bends, with part or all of the bends being firmly connected to an adjacent helical turn by, for example, soldering. In this case, the soldered joint has a smaller release force than the tensile strength of the wire forming the helix. If a ball is fed at one free end of the wire forming the helix, then it is possible to act thereon by hollow forceps and the complete endoprosthesis 1 can be removed again, should this prove necessary. If all the helixes are not interconnected in the above-described manner, the helix length can be adapted to the stenosis region to be treated by compression or drawing apart. In the illustrated embodiment, an applicator 3 may be provided within the sleeve 2, with the applicator 3 being constructed similar to a hollow catheter. The applicator 3 is axially split into several individual tongues 4 at a front end thereof, with the tongues 4 surrounding the endoprosthesis over at least a part of its length, for example, in the illustrated embodiment, over half it length, and be positioned radially between the endoprosthesis 1 and the sleeve 2. The front end of the sleeve 2 may be provided with a roentgen opaque ring. Optionally, within the applicator 3, a counter holder can be provided engaging in the rear region of the endoprosthesis 1.

The supplier or manufacturer assembles the inventive apparatus in this form and the endoprosthesis 1 is supplied radially held in the sleeve 2 to the dealer or doctor.

A first handle 5 is connected to the sleeve 2 and either a fixed or detachable connection may be provided. The applicator 3 is connected to a further handle 6 and either the applicator 3 projects through the handle 5 or an axial attachment 7 projects through the first handle 5. In the illustrated embodiment, the axial attachment 7 is a threadable attachment with a screw thread 8 formed on the outside. The first handle 5 for the sleeve 2 has a corresponding internal thread and is consequently received in a threadable manner along the axial attachment 7 between the first handle 5 and the further handle 6 is provided a blocking element 9, which blocks a relative axial movement between the first and further handles 5, 6. In the illustrated embodiment, the blocking element 9 is in the form of a spacer fashioned as a longitudinally split sleeve, which is mounted on the axial attachment 7. The blocking element 9 is provided with a grip 11 enabling the blocking element 9 to be removed by way of the grip 11 as shown most clearly in FIG. 2.

The applicator 3 and axial attachment 7 are hollow so that the applicator 3 can be engaged over a guide wire or the guide wire can be moved through the parts. An adaptor 12 is provided at the rear end of the further handle 6, with the adaptor 12 enabling connection with further medical instruments such as, for example, syringes, sprays, etc. The first handle 5 is freely rotatably inserted in a ring 13 firmly connected to a guide rod 14 guided in guide members or holders 16 on the further handle 6.

As a result of the construction according to the invention, by means of the further handle 6, the applicator 3 and with it the endoprosthesis 1, following the introduction thereof into a vicinity of a stenosis S, can precisely be held in position while the sleeve 2, by rotating the first handle 5 on the screw thread 8 can be retracted in order to radially release the endoprosthesis 1.

The apparatus according to the invention is used in the following manner. First, a guide wire is introduced into the organ having a stenosis S to be widened. By means of the guide wire the inventive apparatus is introduced into the endoprosthesis 1 held in the sleeve 2 and the applicator 3 until the endoprosthesis 1 comes to rest in a vicinity of the stenosis S in the body vessel or organ K (FIG. 1).

The blocking element 9 between the first and further handles 5, 6 is then removed (FIG. 2). Then, the first handle 5 is threadably advanced on the screw thread 8 of the axial attachment 7, so that the handle 5 and, in particular, the sleeve 2 can be moved axially rearwardly relative to the further handle 6 and the applicator 3 fixed thereto, and the applicator 3 maintains the endoprosthesis 1 in place. The first handle 5 is guided by the ring 13, which is firmly axially connected thereto, but can still rotate, as well as the guide rod 14 fixed thereto, which is held by the guide member or holders 16 on the further handle 6.

If the sleeve 2 is, in this manner, moved axially rearwardly relative to the applicator 3 and the endoprosthesis 1, then the endoprosthesis 1 is successively released. As a result of the heat of the surrounding body vessel or organ K, the endoprosthesis 1 has a tendency to move into its high temperature contour, which is made possible by the retraction of the sleeve 2 and, therefore, enables a radial release, so that the turns or axial portions of the endoprosthesis 1 can successively radially widen (FIG. 3).

If the sleeve 2 also releases the slotted tongues 4 of the applicator 3, then the tongues 4 may also widen the endoprosthesis 1 under the forces acting thereon and engage on the inner wall of the material of the stenosis S. Since the tongues 4 of the applicator 3 still surround the endoprosthesis in this area, the tongues 4 ensure that, as a result of the frictional force on retracting the sleeve 2, the endoprosthesis 1 is not retracted with it and moved out of the area of the stenosis S (FIG. 4). After retracting the sleeve 2 up to the engagement of the first handle 5 on the further handle 6, the path of the two handles 5, 6 precisely correspond to the length of the endoprosthesis 1 in its delivery position, with the length of the endoprosthesis 1 being optionally changeable, in that from the adapter 12 and through the adapter 12 and the sleeve 2 is introduced a slide up to the rear end of the endoprosthesis 1, which is still held in a narrow position. Through the slide it is possible to shorten the length of the endoprosthesis 1, with the shortening occurring in a vicinity of the length of the tongues 4 of the applicator 3. Optionally, the applicator 3 also permits the introduction of forces which act on the rear end of the endoprosthesis 1, that is, the end facing the applicator 3 and, as a result, it can slightly be retracted with the applicator 3 and the endoprosthesis 1 lengthens somewhat in a vicinity of the tongues 4.

Following the desired arrangement and orientation and, in particular, the desired setting of the length of the endoprosthesis 1, it is possible to remove the applicator 3 with its tongues 4. The applicator 3 is axially secured by its parts fixed in the front region of the stenosis S and also by the partial areas engaging between the tongues 4 on the wall of the stenosis S, so that it is not drawn out or undesirably additionally deflected with the removal of the applicator 3 and the tongues 4.

Figure 6:
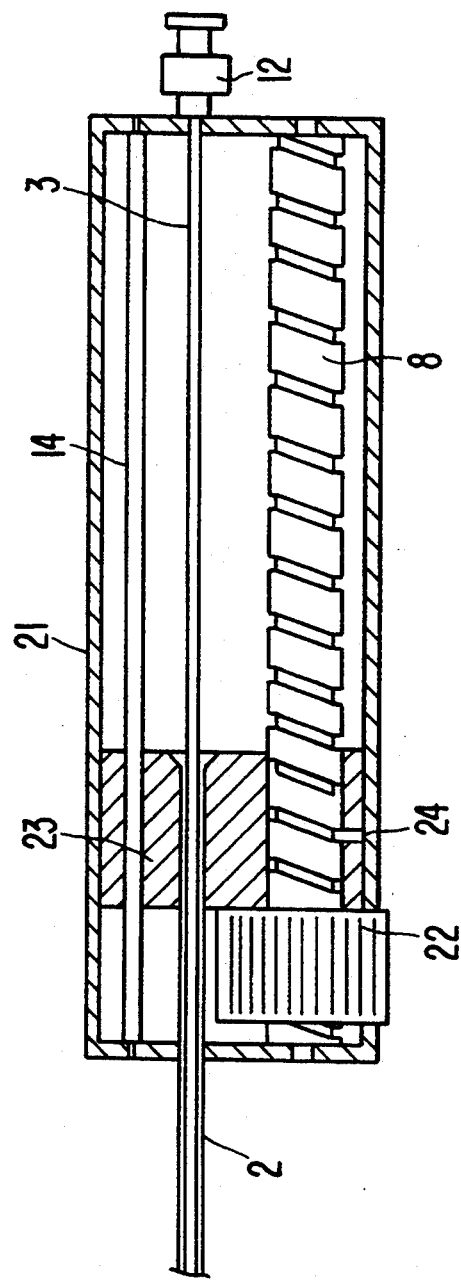
FIG. 6 is a cross sectional view of a dire mechanism for the relative movement of the sleeve to the applicator for the endoprosthesis.

In a construction according to FIG. 6, the handle firmly connected to the applicator 3 is formed by a casing 21, through which the applicator 3 is guided and secured at its rear end by the adaptor 12. A screw thread 8 is mounted in an axially fixed rotary manner in the casing 21. A handle 22, in the form of a narrow wheel 22, is firmly connected to the screw thread 8 and projects laterally somewhat out of the casing 21 and can therefore be operated from the outside. On the screw thread 8 is located a slide or carriage 23 which is guided with a guide pin 24 in the guide groove of the screw thread 8 and the sleeve 2 is fixed to it. For guiding the slide 23 there can also be a guide rod 14 fixed to the casing 21.

If the knurled wheel 22 is now operated from the outside, the screw thread 8 turns and as a result of turning of the screw thread 8, the guide pin 24 guided in its groove, the slide 23 held in a non-rotary manner in the casing 21 is moved axially relative to the casing 21 corresponding to the pitch of the groove and carries the sleeve 2 with it. It moves relative to the applicator 3 and, in the above-described manner, releases its front end and the endoprosthesis 1. In this connection, reference can be made to the embodiment described with respect to FIGS. 1 to 5.

In the embodiment of FIGS. 7 and 8, the inventive apparatus for engaging an endoprosthesis once again includes a sleeve 2 connected or connectable to a first handle 5. Into a guide of the first handle 5 formed by an axial bore, extends an attachment 7 of a further handle 6 carrying the applicator 3 which engages, through the axial bore of the first handle 5 at the sleeve, and extends out of its front end. In the front region of the sleeve 2 is arranged the endoprosthesis 1 in the form of a cylindrical memory metal part, with the applicator 3 also extending through the sleeve 2. In an area within the sleeve 2, the applicator 3 is provided in its rear half with a radial elastic slide portion 31, which can preferably be constructed by tongues similar to the tongues 4 of the embodiment of FIGS. 1–5. The slide portion 31 tapers from the front end to the rear end and, for example, the corresponding tongues at the rear end are firmly connected to the applicator 3, whereas, the front ends are free and can be uprighted radially outwardly so that the engage on or mesh with portions of the endoprosthesis 1.

On the first handle 5 is provided a suction connection 32, which is connected to the interior of the sleeve 2, so that, to the suction connection 32, can be connected a suction device, such as, for example, a syringe, spray or pump, by which liquid and optionally thrombus parts and the like can be suctioned from the front end of the sleeve 2.

The handle 5 is also provided with a blocking element 9 fashioned as a pin which can be radially inserted in the handle 5 and in the axial attachment 7 of the further handle 6, so as to axially block the two handles 5, 6 and therefore also the sleeve 2 and the applicator 3. This is the delivery state of the inventive apparatus. Thus, it is reliably ensured that there is no unintentional sliding of the endoprosthesis 1 out of the sleeve 2 prior to the introduction of the front end of the apparatus into the area of the stenosis S to be widened.

In the illustrated embodiment, the handles 5, 6 are in the form of two gripping rings engageable with the thumb and a finger through a removal-like reciprocating movement, as indicated by the arrows A and B, the handles 5, 6 and, therefore, the sleeve 2 and applicator 3 can be moved axially rearwardly and forwardly relative to one another after removing the blocking element 9. So that the handles 5, 6 can be automatically pressed apart and, therefore, only have to be pressed against one another by the user, a helical spring 34 is located between the handles 5, 6 on a guide bolt 33 and, as a result, the endoprosthesis 1 is automatically moved back into the applicator 3 when the user exerts no force.

The inventive apparatus or sleeve with the endoprosthesis 1 located therein and the applicator 3 extending therethrough can, in a conventional manner, be introduced into the vessel to be widened by, for example, a catheter fitted by the Seldinger guide-wire technique. If the front end of the sleeve 2 is in a vicinity of the stenosis S to be widened or, in particular, the area of the sleeve 2 over which the endoprosthesis 1 extends within it, is located within the stenosis S, following the removal of the blocking element 9, the first handle 5, securing the sleeve 2 can be retracted against the further handle 6. Thus, by means of the further handle 6, the applicator 3 and its slide portion 31, the endoprosthesis 1 can be held in its axial position relative to the sleeve 2, while the front end of the sleeve 2 is partly slid back from the endoprosthesis 1 and, consequently, releases the front end of the endoprosthesis 1 and which can therefore widen within the stenosis S as shown in FIG. 8. The further handle 6 is then retracted somewhat and therefore the first handle is released. As a result, the applicator with the slide portion 31 can also be retracted within the endoprosthesis 1 and the sleeve 2. By virtue of the construction of the slide portion 31 with the described partial conical shape, the slide portion 31 slides within the endoprosthesis 1 and along with the endoprosthesis 1 in a rearward direction, while the endoprosthesis 1 is axially secured within the sleeve 2 due to the higher frictional force. In a further step, the sleeve 2 is retracted again by the first handle 5. Thus, as stated, the free ends of the slide portion 31 are located on the endoprosthesis 1 or engage partially in its meshes or gaps, so that once again they prevent a concomitant retraction of the sleeve 2 and instead maintain the endoprosthesis 1 in its axial position.

This process is repeated until the entire endoprosthesis 1 has been released from the sleeve 2 and is freely located in and widens the area of the stenosis S. The widening of the endoprosthesis 1 takes place by virtue of the fact that it is made of a memory alloy, whose high temperature position is the widened position, whereas, the low temperature position corresponds to a construction which, in FIG. 7 is entirely located within the sleeve 2.

The construction of the inventive apparatus is extremely simple and is easy to use.

We claim:

1. An apparatus for widening a stenosis in a body cavity, the apparatus comprising an endoprosthesis fashioned of a memory alloy and having a substantially cylindrical outer contour, a sleeve surrounding and radially supporting the endoprosthesis, an endoprosthesis applicator for the endoprosthesis adapted to be axially movable in the sleeve, said endoprosthesis being positioned radially between the sleeve and the applicator, and wherein said applicator is provided with a slide portion located within the endoprosthesis, said slide portion projects radially outwardly of the applicator and is adapted to act in an intermediate area of the endoprosthesis for sliding the endoprosthesis out of the sleeve.

2. An apparatus according to claim 1, wherein the slide portion includes tongues axially separated from one another by slots.

3. An apparatus according to claim 2, wherein the tongues include a radially outwardly directed projection.

4. An apparatus according to one of claims 1 or 2, wherein the sleeve is axially movable relative to the applicator.

5. An apparatus according to claim 4, when the sleeve and the applicator are detachably axially blocked against relative movement.

6. An apparatus according to one of claims 1 or 2, wherein means are provided for blocking an axial displacement of the sleeve and the applicator to prevent relative movement, and wherein said means are removable from the apparatus so as to permit axial movement of the sleeve and the applicator.

7. An apparatus according to claim 6, wherein the sleeve and the applicator are respectively connected to handles movable with respect to one another.

8. An apparatus according to one of claims 1 or 2, wherein a first handle is connected to the sleeve and a further handle is connected to the applicator, and wherein an axially extending guide is provided for guiding a movement of the respective handles with respect to each other.

9. An apparatus according to claim 8, wherein a releasable blocking element is positioned between said first handle and said further handle.

10. An apparatus according to claim 8, wherein the locking element is a spacer removeably arranged between said handles.

11. An apparatus according to one of claims 1 or 2, wherein the applicator is hollow over an entire length thereof.

12. An apparatus according to one of claims 1 or 2, wherein the adaptor is provided on a rear end of the applicator.

13. An apparatus according to one of claims 1 or 2, wherein an adaptor is provided on a part fixed to a rear end of the applicator.

14. An apparatus according to one of claims 1 or 2, wherein a suction connection is provided a rear end of the sleeve.

15. An apparatus according to one of claims 1 or 2, wherein a spring forcing a front end of the endoprosthesis into the sleeve is positioned between the endoprosthesis and the sleeve.

* * * * *